(12) United States Patent
Yorkston et al.

(10) Patent No.: US 8,761,340 B2
(45) Date of Patent: Jun. 24, 2014

(54) ACQUISITION OF HIGH SPEED DUAL-ENERGY IMAGES USING A SINGLE PIXILATED DIGITAL DETECTOR

(75) Inventors: John Yorkston, Penfield, NY (US); David H. Foos, Webster, NY (US); Xiaohui Wang, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 878 days.

(21) Appl. No.: 12/239,863

(22) Filed: Sep. 29, 2008

(65) Prior Publication Data
US 2010/0080355 A1    Apr. 1, 2010

(51) Int. Cl.
*H05G 1/64* (2006.01)

(52) U.S. Cl.
USPC ....................... 378/98.11; 378/98.8

(58) Field of Classification Search
USPC .......... 378/98.8, 98.9, 98.11, 98.12, 115–116
See application file for complete search history.

(56) References Cited

U.S. PATENT DOCUMENTS

| | | | |
|---|---|---|---|
| 6,535,579 B1 | 3/2003 | Blake et al. | |
| 6,868,138 B2 | 3/2005 | Clinthorne et al. | |
| 7,005,663 B2 | 2/2006 | Maolinbay et al. | |
| 7,122,802 B2 | 10/2006 | Petrick et al. | |
| 2004/0202281 A1* | 10/2004 | Colbeth et al. | 378/98.8 |
| 2009/0086913 A1* | 4/2009 | Ohta et al. | 378/98.9 |

* cited by examiner

*Primary Examiner* — Hoon Song

(57) ABSTRACT

A method is disclosed for acquiring a high speed dual-energy image pair using a pixilated digital detector. A single pixilated digital detector acquires and encodes two separate images in effectively one image, eliminating the need to read out a first image prior to acquiring a second image. The encoded information is then utilized to obtain two distinct dual-energy images which may be decomposed to form bone and soft-tissue only images.

19 Claims, 7 Drawing Sheets

ACQUISITION OF HIGH SPEED DUAL-ENERGY IMAGES USING A SINGLE PIXILATED DIGITAL DETECTOR

FIELD OF THE INVENTION

The invention relates generally to the field of projection radiography and in particular to the acquisition of dual-energy projection radiographic images. More specifically, the invention relates to a method for acquiring a high speed dual-energy image pair using a pixilated digital detector.

BACKGROUND OF THE INVENTION

In dual-energy imaging, two images of the same object are acquired under different x-ray beam conditions, such as beam energy and filtration. For example, high- and low-energy images of the same object can be acquired. The images can then be decomposed to produce material specific images such as soft-tissue and bone-only images.

One method of acquiring dual-energy images involves double-shot acquisition, in which both the high- and low-energy images are acquired using a single pixilated digital detector. Double-shot acquisition promotes detective quantum efficiency and provides an improved detectability index for dual-energy imaging as compared to sandwiched detectors. Double-shot image acquisition, however, introduces the potential for a decrease in final image quality due to patient motion (e.g. cardiac and respiratory motion) that occurs between the two x-ray exposures. This motion can result in severe artifacts in the final decomposed soft-tissue and bone-only images. Artifacts in the decomposed images decrease the clinical efficacy of the data. As such, it is advantageous to acquire the dual-energy images as close in time as possible.

Standard methods of detector acquisition for dual-energy images involve initiating a first image acquisition, reading out the first image information stored in the detector, and then initiating a second image acquisition. The delay between the acquisition of the first and second image due to the time necessary to read out the first image information prior to initiating the second image acquisition may result in artifacts due to patient motion. Although high-speed detectors are available that minimize the necessary read out time, such detectors are expensive and may be cost prohibitive for certain applications. As such, there is a need to provide a method of acquiring high-speed dual-energy images using a pixilated digital detector which eliminates the delay between image acquisitions as a result of data read out.

SUMMARY OF THE INVENTION

The present invention provides a method of acquiring a high-speed dual-energy image pair using a pixilated digital detector. A voltage is selectively applied to each switch control line in the pixilated digital detector prior to a first x-ray image acquisition such that the signal related to the first x-ray image is acquired in a subset of the pixels in the pixilated digital detector. The voltage applied to a portion of the switch control lines in the pixilated digital detector is then altered prior to a second x-ray image acquisition such that the signal related to the second x-ray image is acquired in each pixel of the pixilated digital detector without readout of the image of the first x-ray exposure. The acquired signals are then read out to the external electronics simultaneously.

In one embodiment of the invention, alternate rows of pixels in the pixilated digital detector acquire the signal related to both the first and second x-ray image, or solely the signal related to the second x-ray image, respectively. The signals from pixels which acquire solely the signal related to the second x-ray image are interpolated to obtain a signal related to the second x-ray image for each pixel in the pixilated digital detector. The signal related to the second x-ray image is then subtracted from each pixel which acquires the signal related to both the first and second x-ray image to obtain a signal related solely to the first x-ray image. The signals from pixels from which the signal from the second x-ray image has been subtracted are interpolated to obtain a signal related to the first x-ray image for each pixel in the pixilated detector.

The signal related to the first x-ray image for each pixel in the pixilated digital detector is converted to obtain a first x-ray image with the original pixel resolution of the pixilated digital detector. The signal related to the second x-ray image for each pixel in the pixilated digital detector is similarly converted to obtain a second x-ray image with the original pixel resolution of the pixilated digital detector. The first and second x-ray images may then be decomposed to obtain either a bone only image or soft tissue only image.

Another embodiment of the present invention provides a method for acquiring a high-speed dual-energy image using a pixilated digital detector wherein the pixilated digital detector is configured such that alternate pixels are connected to alternate switch control lines. A voltage is selectively applied to each switch control line in the pixilated digital detector prior to a first x-ray image acquisition such that the signal related to the first x-ray image is acquired in every other pixel in the pixilated digital detector. The voltage applied to a portion of the switch control lines in the pixilated digital detector is then altered prior to a second x-ray image acquisition such that the signal related to the second x-ray image is acquired in each pixel of the pixilated digital detector. The acquired signals are then read out to the external electronics simultaneously.

Alternate pixels in the pixilated digital detector acquire the signal related to the both the first and second x-ray image, or solely the signal related to the second x-ray image, respectively. The signals from pixels which acquire solely the signal related to the second x-ray image are interpolated to obtain a signal related to the second x-ray image for each pixel in the pixilated digital detector. The signal related to the second x-ray image is then subtracted from each pixel which acquires the signal related to both the first and second x-ray image to obtain a signal related solely to the first x-ray image. The signals from pixels from which the signal from the second x-ray image has been subtracted are interpolated to obtain a signal related to the first x-ray image for each pixel in the pixilated detector.

The signal related to the first x-ray image for each pixel in the pixilated digital detector is converted to obtain a first x-ray image with the original pixel resolution of the pixilated digital detector. The signal related to the second x-ray image for each pixel in the pixilated digital detector is similarly converted to obtain a second x-ray image with the original pixel resolution of the pixilated digital detector. The first and second x-ray images may then be decomposed to obtain either a bone only image or soft tissue only image.

BRIEF DESCRIPTION OF THE DRAWINGS

The foregoing and other objects, features, and advantages of the invention will be apparent from the following more particular description of the embodiments of the invention.

DETAILED DESCRIPTION OF THE INVENTION

The present invention is a method for acquiring high-speed dual-energy images using a pixilated digital detector. In particular, the present invention provides a method whereby a single pixilated digital detector may acquire and encode two separate images in effectively one image, eliminating the need to read out a first image prior to acquiring a second image.

Figure 1:
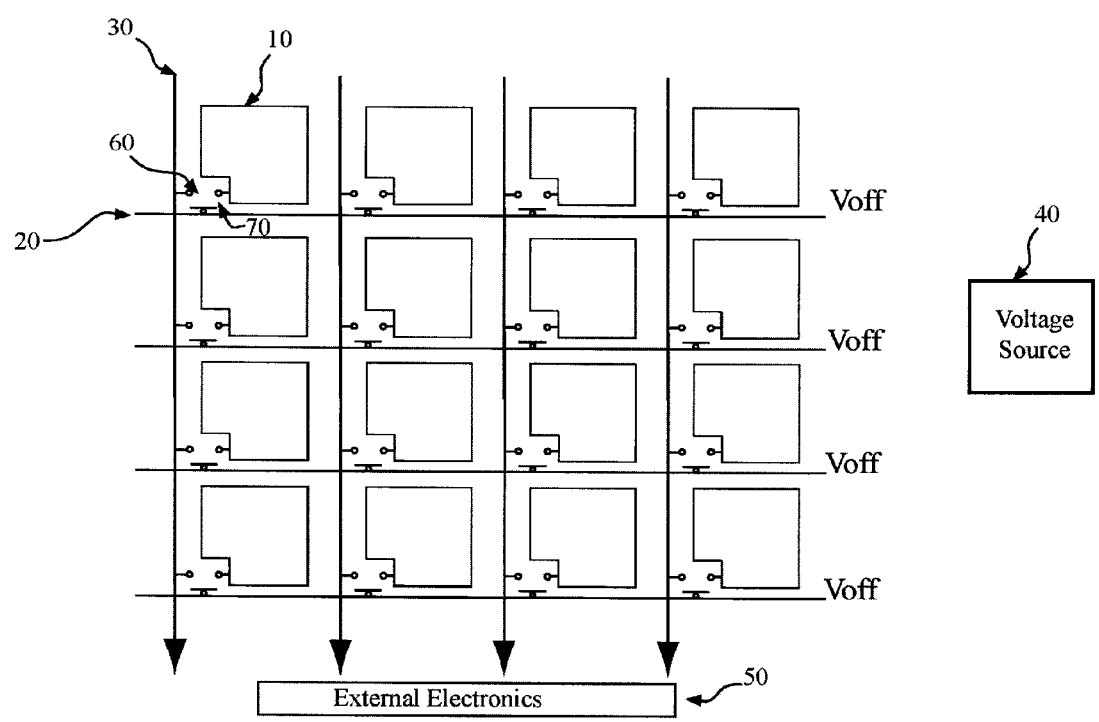
FIG. 1 represents the configuration of an array of pixels in a traditional pixilated digital detector.

FIG. 1 represents the configuration of an array of pixels in a traditional pixilated digital detector such as a digital radiography (DR) detector or a computed radiography (CR) detector. A traditional pixilated digital detector is configured as a rectilinear arrangement of image pixels 10. Each image pixel 10 contains a sensing element that may acquire and store an electrical signal related to an incident x-ray beam. The image pixels 10 are separated along their rows and columns by switch control lines 20 that run perpendicular to data readout lines 30. The switch control lines 20 are connected to a voltage source 40 that can selectively apply a voltage to each switch control line 20. The data-readout lines 30 are connected to external electronics 50 that convert the electrical signal stored in each image pixel 10 into a diagnostic image.

Each individual image pixel 10 is associated with an electrical switch 60. The electrical switch 60 contains a gate 70 that is connected to the switch control line 20. In a typical detector, each electrical switch 60 associated with each image pixel 10 along a specific row of the array is connected to the same switch control line 20. The voltage applied to a switch control line 20 by the voltage source 40 controls the state of each gate 70 connected to that switch control line 20. A voltage may be applied to each switch control line 20 that either holds each gate 70 connected to that switch control line 20 open ($V_{OFF}$) or closed ($V_{ON}$).

When the gate 70 of an electrical switch 60 is open, the image pixel 10 associated with that electrical switch 60 is not connected to the associated data read-out line 30 and is in an acquisition stage. The image pixel 10 acquires and stores an electrical charge related to an incident x-ray beam based on the amount of x-ray transmittance for the object being x-rayed. When a voltage is applied such that the gate 70 of an electrical switch 60 is closed, the image pixel 10 is connected to the associated data read-out line 30 and is in a read-out phase. The electrical charge stored in each image pixel 10 is delivered to the external electronics 50 and converted into a diagnostic image.

Figure 2:
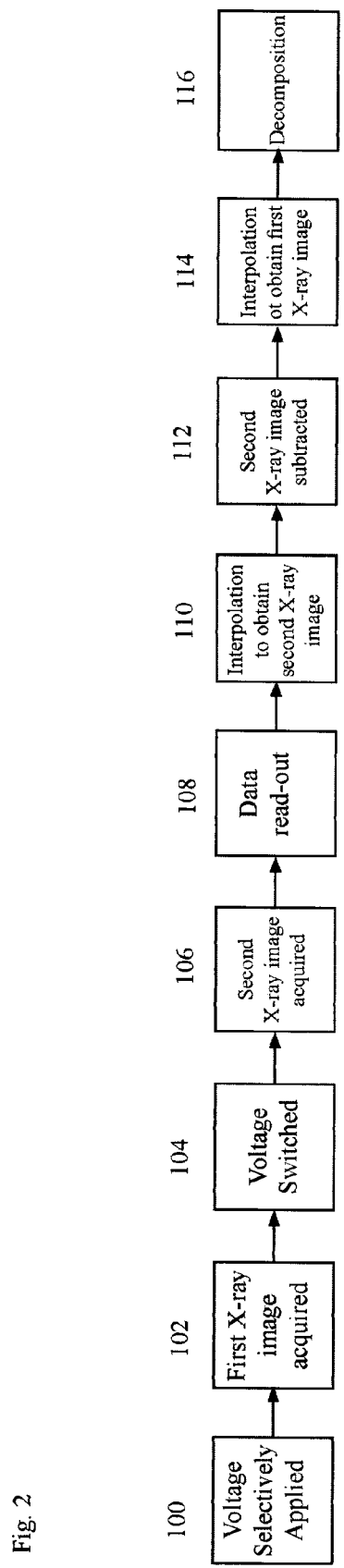
FIG. 2 is a block diagram of one embodiment of the method of acquiring a high-speed dual-energy image pair using a pixilated digital detector.
Figure 3:
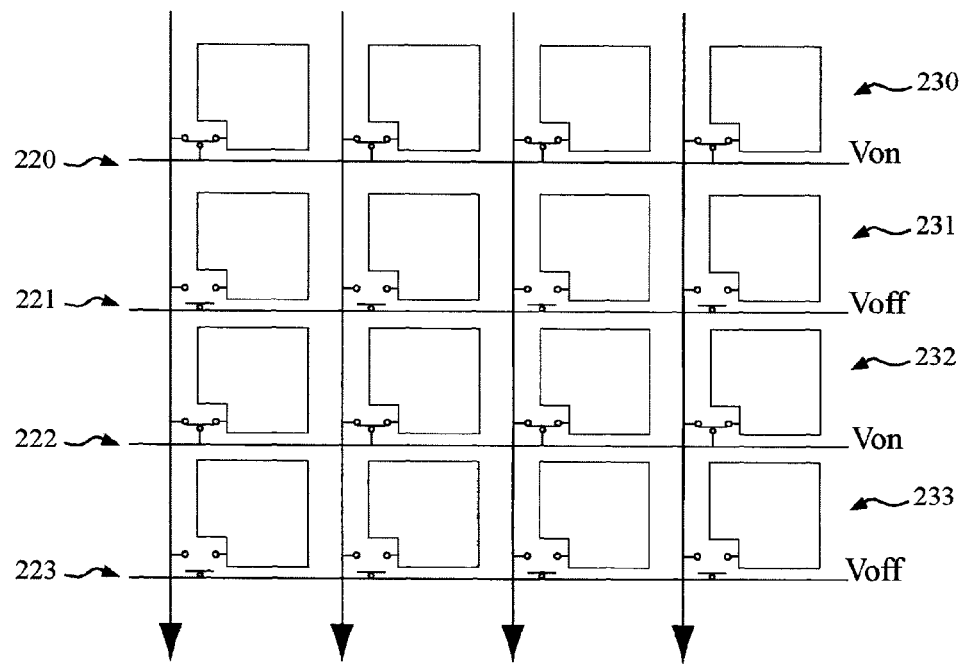
FIG. 3 represents an array of pixels in a traditional pixilated digital detector during the first x-ray image acquisition of the method shown in FIG. 2.

FIG. 2 is a block diagram of one embodiment of the method of acquiring a high-speed dual-energy image pair using a pixilated digital detector. In step 100 a voltage is selectively applied to each switch control line such that the gates of the electrical switches on alternate switch control lines are held open and closed, respectively. In step 102 a first x-ray image is acquired. FIG. 3 represents an array of pixels in a traditional pixilated digital detector during the first x-ray image acquisition in step 102 as a result of the voltage applied in step 100 of the method shown in FIG. 2. Switch control lines 220 and 222 are held at a voltage ($V_{ON}$) such that the gates of the electrical switches connected to switch control lines 220 and 222 are closed. Image pixel rows 230 and 232 are in a read-out phase and do not acquire any information related to the first x-ray image. Alternate switch control lines 221 and 223 are held at a voltage ($V_{OFF}$) such that the gates of the electrical switches connected to switch control lines 221 and 223 are open. Image pixel rows 231 and 233 are in an acquisition phase and acquire and store information related to the x-ray transmittance of the first x-ray image acquisition.

Referring again to FIG. 2, in step 104 the voltage is switched such that all gates of the electrical switches are open and each image pixel in the digital detector is in an acquisition phase. The voltage may be changed very quickly and no data read-out takes place. In step 106 a second x-ray image is acquired.

Figure 4:
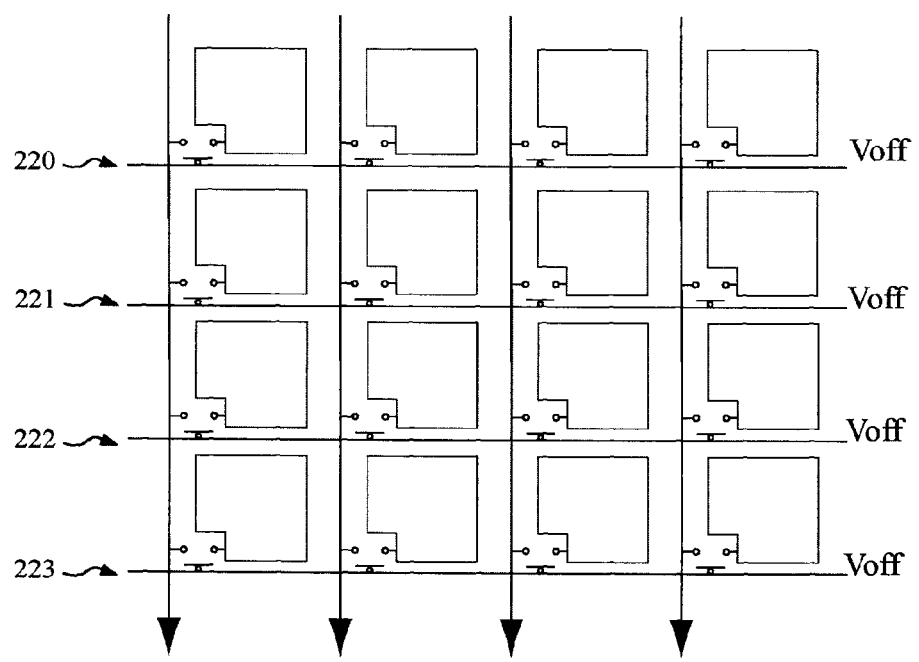
FIG. 4 represents an array of pixels in a traditional pixilated digital detector during the second x-ray image acquisition of the method shown in FIG. 2.

FIG. 4 represents an array of pixels in a traditional pixilated digital detector after the voltage is switched in step 104 and during the second x-ray image acquisition in step 106 of the method shown in FIG. 2. The voltage applied to switch control lines 220 and 222 is switched to a voltage ($V_{OFF}$) such that the gates of the electrical switches connected to switch control lines 220 and 222 are open. Switch control lines 221 and 223 are maintained at a voltage ($V_{OFF}$) such that the gates of the electrical switches connected to switch control lines 221 and 223 remain open. The entire array of pixels in the digital detector is in an acquisition phase. Each pixel acquires and stores information related to the x-ray transmittance of the second x-ray image acquisition.

Figure 5:
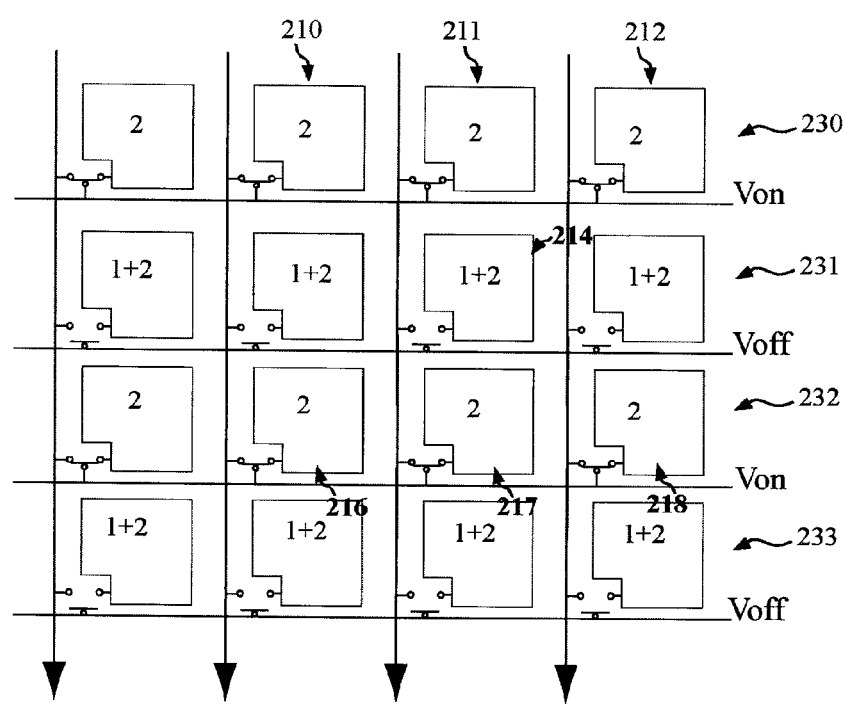
FIG. 5 represents the image information stored in the image pixels after the second x-ray image acquisition of the method shown in FIG. 2.

FIG. 5 represents the image information stored in the image pixels after the second x-ray image acquisition in step 106 of the method shown in FIG. 2. After the second x-ray image acquisition, image pixel rows 230 and 232 contain only information related to the second x-ray image acquisition while the image pixel rows 231 and 233 contain information related to both the first and second x-ray image acquisitions. Referring again to FIG. 2, in step 108 the data stored in the pixilated detector is read out to the external electronics by applying a voltage ($V_{ON}$) to each switch control line. The data read-out may occur in the traditional manner on a line-by-line basis.

In step 110, the image information related to the second x-ray image in the image pixels in rows which contain only information related to the second x-ray image is interpolated to acquire an image value related to the second x-ray image for each pixel in the detector and to regain the original pixel resolution for the second x-ray image. For example, referring again to FIG. 5, the signals integrated in image pixels 210, 211, 212, 216, 217, and 218 related to the second x-ray image acquisition, or any weighted combination of image information contained in the surrounding pixels, may be interpolated to obtain a value for the second x-ray image acquisition for image pixel 214.

Referring again to FIG. 2, in step 112 the interpolated values for the second x-ray image are subtracted from the image information stored in the image pixels in the rows which contain information related to both the first and second x-ray image, such as image pixel rows 231 and 233 in FIG. 5, to obtain a value related solely to the first x-ray image. In step 114 the values related to the first x-ray image are interpolated to acquire an image value related to the first x-ray image for each pixel in the detector and to regain the original pixel resolution for the first x-ray image. In step 116 the acquired first and second x-ray images may be decomposed to form a bone-only or soft-tissue image.

Figure 6:
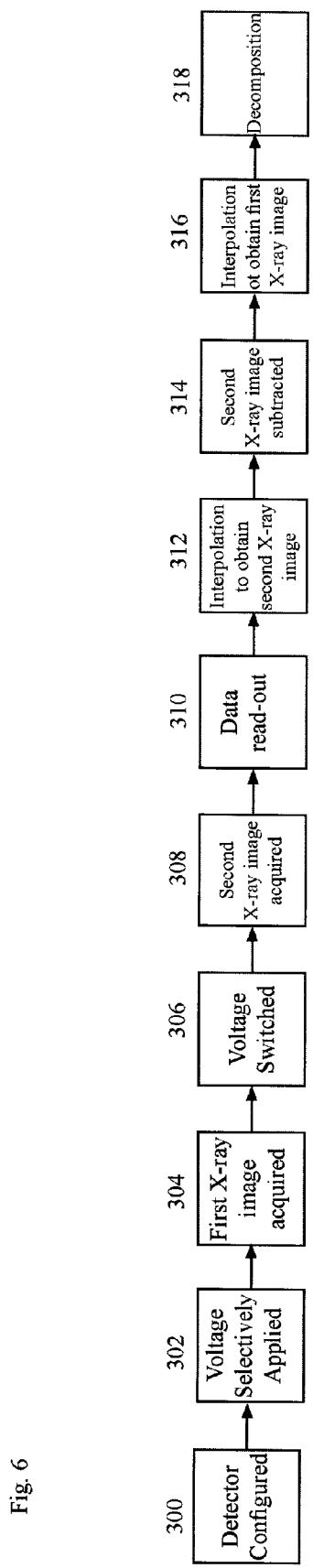
FIG. 6 is a block diagram of the preferred embodiment of the method of acquiring a high-speed dual-energy image pair using a pixilated digital detector.

FIG. 6 is a block diagram of the preferred embodiment of the method of acquiring a high-speed dual-energy image pair using a pixilated digital detector of the present invention. In step 300 the pixilated digital detector is configured such that alternate image pixels along a row are connected to alternate switch control lines. In step 302 a voltage is selectively applied such that alternate switch control lines are held at $V_{OFF}$ and $V_{ON}$, respectively. As such, the image pixels having electrical switches located along the switch control lines held at $V_{OFF}$ will be in an acquisition stage while image pixels having electrical switches located along switch control lines held at $V_{ON}$ will be in a read-out phase. In step 304 a first x-ray image is acquired.

Figure 7:
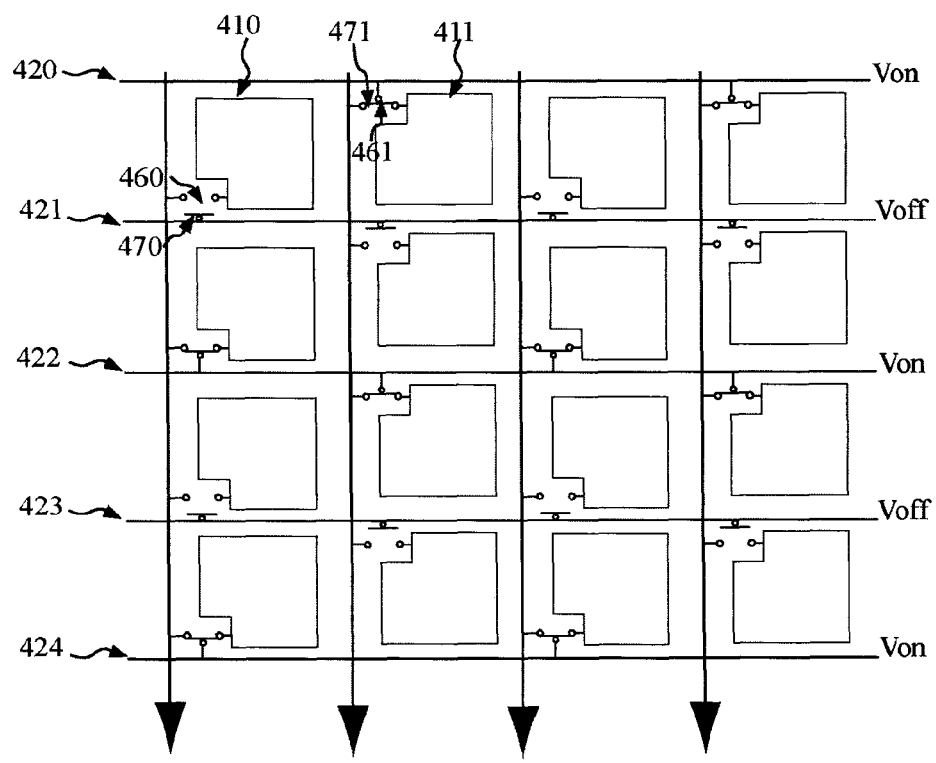
FIG. 7 represents an array of pixels in the reconfigured pixilated digital detector during the first x-ray image acquisition of the method shown in FIG. 6.

FIG. 7 represents an array of pixels in the reconfigured pixilated digital detector during the first x-ray image acquisition in step 304 as a result of the voltage applied in step 302 of the method shown in FIG. 6. Alternate image pixels, such as image pixels 410 and 411, have electrical switches 460 and 461 with gates 470 and 471 which are connected to alternate switch control lines 420 and 421, respectively. Switch control lines 420, 422, and 424 are held at a voltage ($V_{ON}$) such that the gates of the electrical switches connected to switch control lines 420, 422, and 424 are closed. The image pixels with gates connected to switch control lines 420, 422, and 424 are in a read-out phase and do not acquire any information related to the first x-ray image. Alternate switch control lines 421 and 423 are held at a voltage ($V_{OFF}$) such that the gates of the electrical switches connected to switch control lines 421 and 423 are open. The image pixels with gates connected to switch control lines 421 and 423 are in an acquisition phase and acquire and store information related to the x-ray transmittance of the first x-ray image acquisition.

Figure 8:
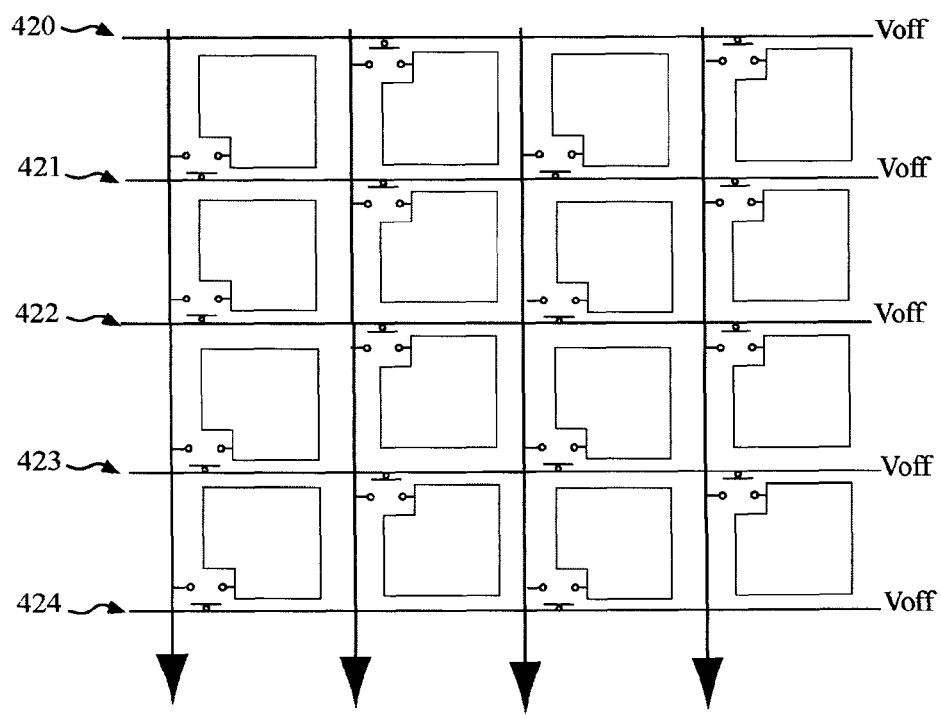
FIG. 8 represents an array of pixels in the reconfigured pixilated digital detector during the second x-ray image acquisition of the method shown in FIG. 6.

Referring again to FIG. 6, in step 306 the voltage is switched such that all gates of the electrical switches are open and each image pixel in the digital detector is in an acquisition phase. The voltage may be changed very quickly and no data read-out takes place. In step 308 a second x-ray image is acquired. FIG. 8 represents an array of pixels in the reconfigured pixilated digital detector after the voltage is switched in step 306 and during the second x-ray image acquisition in step 308 of the method shown in FIG. 6. The voltage applied to switch control lines 420, 422, and 424 is switched to a voltage ($V_{OFF}$) such that the gates of the electrical switches connected to switch control lines 420, 422, and 424 are open. Switch control lines 421 and 423 are maintained at a voltage ($V_{OFF}$) such that the gates of the electrical switches connected to switch control lines 421 and 423 remain open. The entire array of image pixels in the digital detector is in an acquisition phase. Each pixel acquires and stores information related to the x-ray transmittance of the second x-ray image acquisition.

Figure 9:
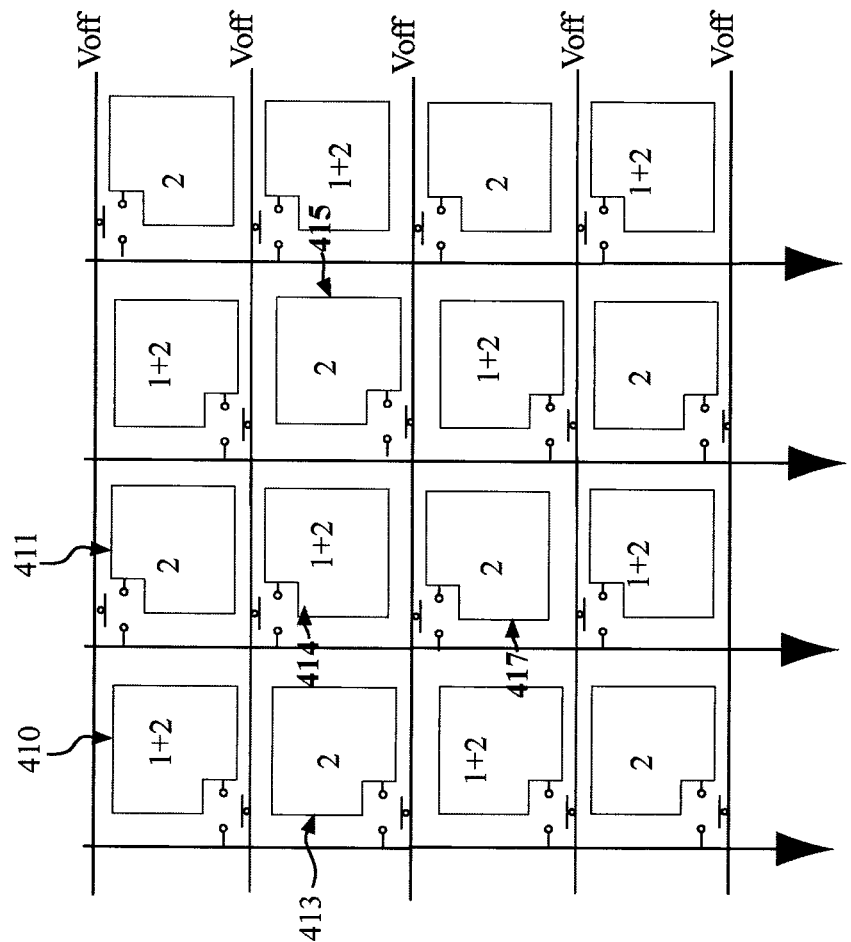
FIG. 9 represents the image information stored in the pixels after the second x-ray image acquisition of the method shown in FIG. 6.

FIG. 9 represents the image information stored in the pixels after the second x-ray image acquisition in step 308 of the method shown in FIG. 6. Alternate image pixels are integrated with either image information related to both the first and second x-ray acquisition, or solely the second x-ray acquisition. For example, image pixel 410 is integrated with information related to both the first and second x-ray acquisitions, while image pixel 411 is integrated solely with a signal related to the second x-ray acquisition. Referring again to FIG. 6, in step 310 the data stored in the pixilated detector is read out to the external electronics by selectively applying a voltage ($V_{ON}$) to each switch control line. The data read-out may occur in the traditional manner on a line-by-line basis.

In step 312 the image information related to the second x-ray image in the image pixels which contain only information related to the second x-ray image is interpolated to acquire an image value related to the second x-ray image for each pixel in the detector and to regain the original pixel resolution for the second x-ray image. For example, referring again to FIG. 9, the signals integrated in image pixels 411, 413, 415, and 417 related to the second x-ray image acquisition, or any weighted combination of image information contained in the surrounding pixels, may be interpolated to obtain a value for the second x-ray image acquisition for image pixel 414.

Referring again to FIG. 6, in step 314 the interpolated values calculated for the second x-ray image are subtracted from the image information stored in the image pixels which contain information related to both the first and second x-ray image, such as image pixel 414 in FIG. 9, to obtain a value related solely to the first x-ray image for those image pixels. In step 316 the values related to the first x-ray image calculated in step 314 are interpolated to acquire an image value related to the first x-ray image for each image pixel in the detector and to regain the original pixel resolution for the first x-ray image. In step 318 the acquired first and second x-ray images may be decomposed to form a bone-only or soft-tissue image.

A computer program product may include one or more storage medium, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice the method according to the present invention.

While illustrative embodiments have been presented and described, it will be clear to those proficient in the art that various changes can be made therein without departing from the spirit and scope of the invention.

What is claimed is:

1. A method for acquiring a high-speed dual-energy image pair using a pixilated digital detector comprising:
   selectively applying a voltage to each switch control line in the pixilated digital detector prior to a first x-ray image acquisition;
   acquiring a signal related to a first x-ray image;
   altering the voltage applied to a portion of the switch control lines in the pixilated digital detector prior to a second x-ray image acquisition;
   acquiring a signal related to a second x-ray image; and
   reading out the acquired signals simultaneously, wherein:
   the voltage is selectively applied such that the signal related to the first x-ray image is acquired in at least first and second non-adjacent pixels in the pixilated digital detector; and
   the voltage is altered prior to the second image acquisition such that the signal related to the second x-ray image is acquired in a plurality of adjacent pixels of the pixilated digital detector, the plurality of adjacent pixels including the first pixel and the second pixel.

2. The method of claim 1 wherein:
the voltage is selectively applied such that the signal related to the first x-ray image is acquired in a plurality of rows, wherein the plurality of rows comprise every other row of pixels in the pixilated digital detector; and
the voltage is altered prior to the second image acquisition such that the signal related to the second x-ray image is acquired in a plurality of adjacent rows of the pixilated digital detector.

3. The method of claim 2 wherein:
alternate rows of pixels in the pixilated digital detector acquire the signal related to the both the first and second x-ray image, or solely the signal related to the second x-ray image, respectively.

4. The method of claim 3 further comprising:
interpolating the signals from pixels which acquire solely the signal related to the second x-ray image to obtain a signal related to the second x-ray image for each pixel in the pixilated digital detector;
subtracting the signal related to the second x-ray image from each pixel which acquires the signal related to both the first and second x-ray image to obtain a signal related solely to the first x-ray image; and
interpolating the signals from pixels from which the signal from the second x-ray image has been subtracted to obtain a signal related to the first x-ray image for each pixel in the pixilated detector.

5. The method of claim 4 further comprising:
converting the signal related to the first x-ray image for each pixel in the pixilated digital detector to obtain a first x-ray image with the original pixel resolution of the pixilated digital detector; and
converting the signal related to the second x-ray image for each pixel in the pixilated digital detector to obtain a second x-ray image with the original pixel resolution of the pixilated digital detector.

6. The method of claim 5 further comprising:
wherein the interpolated pixels comprise any weighted combination of image information stored in surrounding pixels of the interpolated pixels or stored in nearby pixels of the interpolated pixels.

7. The method of claim 5 further comprising:
decomposing the first and second x-ray images to obtain a soft-tissue only image or a bone only image.

8. The method of claim 1 comprising configuring the pixilated digital detector such that alternate pixels are connected to alternate switch control lines; wherein:
the voltage is selectively applied such that the signal related to the first x-ray image is acquired in a plurality of alternate pixels in the pixilated digital detector; and
the voltage is altered prior to the second image acquisition such that the signal related to the second x-ray image is acquired in a continuous set of pixels in a row of the pixilated digital detector.

9. The method of claim 8 wherein:
alternate pixels in the pixilated digital detector acquire the signal related to the both the first and second x-ray image, or solely the signal related to the second x-ray image, respectively.

10. The method of claim 9 further comprising:
interpolating the signals from pixels which acquire solely the signal related to the second x-ray image to obtain a signal related to the second x-ray image for each pixel in the pixilated digital detector;
compensating the signal related to the second x-ray image from each pixel which acquires the signal related to both the first and second x-ray image to obtain a signal related solely to the first x-ray image; and
interpolating the signals from pixels from which the signal from the second x-ray image has been compensated to obtain a signal related to the first x-ray image for each pixel in the pixilated detector.

11. The method of claim 10 further comprising:
converting the signal related to the first x-ray image for each pixel in the pixilated digital detector to obtain a first x-ray image with the original pixel resolution of the pixilated digital detector; and
converting the signal related to the second x-ray image for each pixel in the pixilated digital detector to obtain a second x-ray image with the original pixel resolution of the pixilated digital detector, wherein the compensating comprises subtracting.

12. The method of claim 11 further comprising:
decomposing the first and second x-ray images to obtain a bone only image.

13. The method of claim 11 further comprising:
decomposing the first and second x-ray images to obtain a soft-tissue only image.

14. A method for acquiring a high-speed dual-energy image pair using a pixilated digital detector comprising:
exposing an X-ray receptor to a first X-ray radiation time interval;
capturing first image data in a first subset of pixels of the X-ray receptor during the first X-ray radiation time interval;
exposing the X-ray receptor to a second X-ray radiation time interval;
capturing second image data in a second subset of pixels of the X-ray receptor during the second X-ray radiation time interval;
reading out the captured first image data and the captured second image data in a single signal from the second subset of pixels, wherein the first subset of pixels are a subset of the second subset of pixels, the first subset of pixels being less than all of the second subset of pixels;
interpolating the signals from pixels which acquire solely the signal related to the second x-ray image to obtain a signal related to the second x-ray image for each pixel in the pixilated digital detector;
modifying the signal related to the second x-ray image from each pixel that acquires the signal related to both the first and second x-ray image to obtain a signal related solely to the first x-ray image; and
interpolating the signals from pixels from which the signal from the second x-ray image has been modified to obtain a signal related to the first x-ray image for each pixel in the pixilated detector.

15. The method of claim 14 wherein the first subset of pixels comprise non-adjacent pixels.

16. The method of claim 15 wherein the first subset of pixels comprise alternate pixels, interspersed pixels, alternate rows, interspersed rows, alternate columns or interspersed columns, and wherein the second X-ray radiation time interval uses different beam conditions than the first X-ray radiation time interval.

17. A method for acquiring a high-speed dual-energy image pair using a pixilated digital detector comprising:
exposing an X-ray receptor to first X-ray radiation during a first time interval;
acquiring first image data for the first time interval in a first subset of pixels of the X-ray receptor;

exposing the X-ray receptor to second X-ray radiation during a second different time interval;

acquiring second image data for the second time interval in a second subset of pixels of the X-ray receptor, wherein the second subset of pixels is different than the first subset of pixels; and performing a single readout of the pixilated digital detector to output both the acquired first image data in the first subset of pixels of the X-ray receptor and the acquired second image data in the second subset of pixels of the X-ray receptor simultaneously, and wherein the first subset of pixels and the second subset of pixels are not read out between the first time interval and the second time interval.

18. The method of claim 17 wherein the first subset of pixels comprise non-adjacent pixels, and wherein the second X-ray radiation uses different beam conditions than the first X-ray radiation.

19. A method for acquiring a high-speed dual-energy image pair using a pixilated digital detector comprising:

selectively storing an electrical charge related to a first incident x-ray in less than all of pixels in a portion of the pixilated digital detector;

storing an electrical charge related to a second incident x-ray in the pixels in the portion of the pixilated digital detector; and reading out the pixels in the portion of the pixilated digital detector to acquire both the selectively stored electrical charge resulting from the first incident x-ray and the stored electrical charge resulting from the second incident x-ray at the same time, where the second incident x-ray properties are different than the first incident x-ray properties.

* * * * *